United States Patent [19]

Kawahara

[11] Patent Number: 5,294,553
[45] Date of Patent: Mar. 15, 1994

[54] METHOD FOR THE GRAVIMETRIC DETERMINATION OF OIL AND GREASE

[75] Inventor: Fred K. Kawahara, Burlington, Ky.

[73] Assignee: The United States of America as represented by the Administrator of the Environmental Protection Agency, Washington, D.C.

[21] Appl. No.: 66,474

[22] Filed: May 26, 1993

Related U.S. Application Data

[63] Continuation-in-part of Ser. No. 43,385, Apr. 6, 1993, abandoned.

[51] Int. Cl.$^5$ .................... G01N 31/00; G01N 33/03; G01N 33/20
[52] U.S. Cl. .................................. 436/60; 436/8; 73/152; 73/153
[58] Field of Search ............... 252/408.1; 436/8, 60; 73/152, 153

[56] References Cited

U.S. PATENT DOCUMENTS

| | | | |
|---|---|---|---|
| 4,279,664 | 7/1981 | Figiel et al. | 134/38 |
| 4,399,693 | 8/1983 | Gournay | 73/152 |
| 4,549,966 | 10/1985 | Beall | 210/661 |
| 4,654,160 | 3/1987 | Wilson et al. | 134/42 |
| 4,810,414 | 3/1989 | Huge-Jensen et al. | 252/174.12 |
| 4,997,243 | 12/1990 | Barder et al. | 530/208 |
| 5,092,983 | 3/1992 | Eppig et al. | 208/317 |
| 5,118,438 | 6/1992 | Magid et al. | 252/172 |
| 5,128,864 | 6/1993 | Pennybaker | 73/152 |

FOREIGN PATENT DOCUMENTS 56-124389 9/1981 Japan.

OTHER PUBLICATIONS

The Clean Water Act (CWA) Method 413.1, "Oil and Grease, Total, Recoverable", USEPA, Environmental Monitoring and Support Laboratory, Cincinnati, Ohio 1974.
Standard Method 5520 "Oil and Grease", Standard Methods for the Examination of Water and Wastewater, 17th Ed. (1989), pp. 5-41—5-48.
Kirschman, et al., "Determination of Oil in Oil-Field Waste Waters", Anal. Chem 21, pp. 793-797 (1949).
Gilcreas, F. W., et al., "Two New Methods for the Determination of Grease in Sewage", Sewage and Industrial Wastes, 25, [12] 1379-1390 (1953).
Resource Conservation and Recovery Act Methods (RCRA) 9070A "Total Recoverable Oil and Grease (Gravimetric, Separatory Funnel Extraction)", Rev. 1, Nov. 1990.
Resource Conservation and Recovery Act Methods (RCRA) 9071A "Oil and Grease Extraction Method for Sludge Samples", Rev. 1, Nov. 1990.
Taras et al., "Determination of Emulsifying Oil in Industrial Wastewater", JWPCF Research Suppl., 40, R404-R411 (1968).
Method 502A in "Standard Methods for the Examination of Water and Wastewater," 14th ed., pp. 515-516.
Dr. F. Kawahara, "A Study to Select the Most Suitable Replacement Solvent for Freon 1,1,3 for the Gravimetric Determination of Oil and Grease", Environmental Monitoring Systems Laboratory, 20 pages.
Kawahara, "Study to Determine A Suitable Substitute for Freon 113 in the Gravimetric Analysis of Oil and Grease in Waters".

Primary Examiner—James C. Housel
Assistant Examiner—N. Bhat
Attorney, Agent, or Firm—Spencer, Frank & Schneider

[57] ABSTRACT

A non-halogenated solvent mixture for gravimetric determination of grease and oil in an aqueous or a solid matrix comprising a mixture of n-hexane and methyl tertiary-butyl ether present in a volume ratio of 80% to 20% respectively. A method of gravimetric determination of grease and oil in an aqueous or a solid matrix which comprises preparing a sample; extracting the same using this non-halogenated solvent mixture; distilling; evaporating and weighing the extraction residue.

8 Claims, 1 Drawing Sheet

METHOD FOR THE GRAVIMETRIC DETERMINATION OF OIL AND GREASE

This application is a continuation-in-part application of prior filed, copending U.S. patent application, Ser. No. 8/043,385 filed Apr. 6, 1993, now abandoned.

FIELD OF THE INVENTION

The present invention relates to a novel solvent composition which can replace an environmentally damaging chlorofluorocarbon in analytical methods, and more particularly for use in United States Environmental Protection Agency's approved methods for determining oil and grease.

TECHNOLOGY REVIEW

The knowledge of the quantity of oil and grease present in wastewater systems is helpful in the proper design and operation of wastewater treatment systems. It is known that in the determination of oil and grease, the absolute quantity of substances with similar physical characteristics are measured quantitatively on the basis of their common solubility in an organic solvent.

Specifically, 1,1,2-trichloro-1,2,2-trifluoroethane, available from E.I duPont de Nemours & Co. as FREON ® 1,1,3 chlorofluorocarbon, has been widely utilized as an effective agent useful in the determination of grease and oil because of its solvent power for greases, oils, waxes and the like.

The value of any analytical method chosen as a standard for the estimation of oil and grease can be determined only by correlating analytical results with the actual wastewater treatment practice. Certain constituents, such as fatty acids, glycerides, greases, and waxes when present in excessive amounts, may influence the efficient treatment in wastewater operations.

When the grease-like constituents attain a high level (e.g. 50 mg/L) in wastewaters, grease balls are formed and must be gathered at the settling tanks. These are skimmed and transferred to a landfill. It has been estimated that approximately 160 cubic feet of grease per day are encountered in one sewage treatment facility having a 130 million gallon per day treatment system. Proper design and efficient operations for wastewater treatment systems are essential for the ecological well being of the country.

Various methods for determination of oil and grease are known. Some of the U.S. Environmental Protection Agency's established tests to determine oil and grease in waste samples are as follows.

The Clean Water Act (CWA) Method 413.1, in "Methods for Chemical Analysis of Water and Wastes", 1979, U.S. Environmental Protection Agency, Environmental Monitoring and Support Laboratory, Cincinnati, Ohio 45268 (1983), or "Oil and Grease, Total, Recoverable" (issued 1974) which discloses the determination of oil and grease on surface water by the gravimetric technique.

Standard Method 5520 "Oil and Grease", *Standard Methods for the Examination of Water and Wastewater,* 17th Edition, Section 5520 (1989), which discloses use of silica gel for clean up and the removal of polar fatty materials and also the extraction method for soil and sludges and so forth in addition to the gravimetric method.

Kirschman, H. D. and Pomeroy, R., "Determination of Oil in Oilfield Waste Waters," *Anal. Chem.* 21, 793, (1949) which teaches a method involving two procedures: the wet extraction procedure and the flocculation procedure.

Gilcreas, F. W., Sanderson, W. W. and Elmer, R. P. "Two New Methods for the Determination of Grease in Sewage, *Sewage and Industrial Wastes* 25, [12] 1379, (1953), discloses the Sanderson method of homogenization of the oil sample and extraction: (1) direct extraction method, (2) semi-wet extraction method. This reference indicates that the efficiency of the extraction method is dependent on the number of extractions utilized.

Resource Conservation and Recovery Act Methods (RCRA) 9070A "Total Recoverable Oil and Grease (Gravimetric, Separatory Funnel Extraction", and 9071A, "Oil and Grease Extraction Method for Sludge Samples" Rev. 1, Nov. 1990. EPA Document Number SW-846. These methods involve determination of oil and grease in sludge and soil samples.

Taras, M. J., et al., "Determination of Emulsifying Oil in Industrial Wastewater," JWPCF Research Suppl., 40, R404 (1968) discloses determination of emulsion oil which is further treated for suitable extraction.

Method 502A (1075) in "Standard Methods for the Examination of Water and Wastewater", 14th ed., p. 515, or "Partition-Gravimetric Method" involves a partition gravimetric method which has been used, employing sodium sulfate and vacuum drying of samples. (This addition, however, will cause sodium sulfate to appear in the dried residue of the emulsion samples.)

The extraction solvent, 1,1,2-trichloro-1,2,2-trifluoroethane has been used by the U.S. Environmental Protection Agency in the gravimetric determination of oil and grease. However, 1,1,2-trichloro-1,2,2-trifluoroethane is one of the halogenated chlorofluorocarbons which is currently suspected of attacking and decomposing stratospheric ozone. The U.S.E.P.A., consequently, set out to find a suitable replacement solvent for 1,1,2-trichloro-1,2,2-trifluoroethane for use in the gravimetric determination of oil and grease. See: Kawahara, F. K., "A Study to Select the Most Suitable Replacement Solvent for Freon-113 for the Gravimetric Determination of Oil and Grease," U.S. Environmental Protection Agency, Environmental Monitoring and Support Laboratory, Cincinnati, Ohio. This study involved mixtures of the solvents used in the present invention with different ranges of concentrations.

Liquid-liquid extraction is a separation process that depends on the transfer of components to be separated from one liquid phase into a second liquid phase that is immiscible with the first. After attaining equilibrium, there is a distribution of compounds between the two phases dependent upon the distribution coefficient of the compounds in each phase.

In this case, the extracted oil and grease are transferred from the water phase into the organic phase by use of proper solvents that are sufficiently polar but immiscible in the water phase.

The physical and chemical properties of polar compounds are intermediate between those of the high-melting, highly reactive ionic compounds and those of the low-boiling, relatively inert non-polar substances. As the polarity changes, there is a gradual merging of these intermediate polar compounds into the two groups, i.e., reactive, ionic compounds and non-polar hydrocarbons. The polarity of a compound is a function of its dielectric constant, $\epsilon$, which is the product of the charges and the distance between the two average centers of positive and negative electricity. In the case of alcohols, for example, as the hydrocarbon portion increases, there is a continuous decrease in the dielectric constant from methyl alcohol ($\epsilon=31$) to octyl alcohol ($\epsilon=3.4$).

Non-polar solvents generally dissolve only non-polar compounds, because these solvents do not have the strong dipoles which are necessary to break down or dissolve the powerful interionic attractions of a crystal lattice, or to form associative complexes with the solute, or in some cases to cleave a covalent bond to produce ionized species. As a rule, the non-polar solvents are able to dissolve and separate other non-polar solutes that have low intermolecular forces of attraction, resulting in the solution of solute.

Greases, residual fuel oils, asphaltic feed stock, and certain petroleum jellies are only partially soluble in hexane because their strong intermolecular cohesive forces prevent solution in a non-polar solvent. To dissolve these products and high molecular weight constituents such as carboids in asphalt, the intermolecular forces must be overcome by somewhat polar solvents. Thus, the selection of solvents with somewhat higher dielectric constants and with capability to separate the intermolecular, associative forces is necessary.

Many solvent and azeotrope-like mixtures are useful as degreasing agents. For example, U.S. Pat. No. 4,279,664, Fifiel et al., entitled AZEOTROPE-LIKE COMPOSITIONS OF TRICHLOROTRIFLUOROETHANE, ACETONE AND N-HEXANE describes an azeotrope-like composition consisting essentially of 1,1,2 trichloro-1,2,2- trifluoroethane, acetone and n-hexane having utility as degreasing agents and as solvents to remove polymeric binders containing inks, such as carbon black which are used in copy machines.

U.S. Pat. No. 4,654,160, Wilson et al., entitled AZEOTROPE-LIKE COMPOSITIONS OF TRICHLOROTRIFLUOROETHANE, METHANOL, ACETONE, NITROMETHANE AND HEXANE discloses an azeotrope-like composition comprising trichlorotrifluoroethane, methanol, acetone, nitromethane and hexane which are stable and have utility as vapor degreasing agents and as solvents in a variety of industrial cleaning applications including the defluxing of printed circuit boards.

U.S. Pat. No. 4,973,362, Magid et al., entitled AZEOTROPE-LIKE COMPOSITIONS OF 1,1,2-TRICHLORO-1,2,2-TRIFLUOROETHANE, METHANOL, NITROMETHANE, 1,2-DICHLOROETHYLENE AND HEXANE describes an azeotrope-like composition comprising 1,1,2-trichloro-1,2,2-trifluoroethane, methanol, nitromethane, 1,2-dichloroethylene and hexane useful in a variety of vapor degreasing applications and as solvents in a variety of industrial cleaning applications including defluxing of printed circuit boards.

U.S. Pat. No. 5,118,438, Magid et al., entitled AZEOTROPE-LIKE COMPOSITIONS OF DICHLOROPENTAFLUOROPROPANE AND A HYDROCARBON CONTAINING SIX CARBON ATOMS discloses stable azeotrope-like composition consisting essentially of dichloropentafluoropropane and a hydrocarbon containing six carbon atoms which are useful in a variety of industrial cleaning applications including cold cleaning and defluxing of printed circuit boards.

These collected patents show combinations of chlorofluorocarbon compounds not unlike 1,1,2-trichloro-1,2,2-trifluoroethane and several varieties of hexane compounds, with or without other reagents, as azeotropic compositions having utility as solvents, degreasing agents and industrial cleaners and defluxing agents. They are representative of the present state of the art relating to solvent mixtures containing either hexane or a hexane isomer.

Nor do organic extraction solvents suggest the present invention. For example, U.S. Pat. No. 4,977,243 to Timothy Barder, et al. entitled SEPARATION OF STEROLS FROM LOW-ACID FEEDS WITH MAGNESIUM SILICATE AND METHYL-TERT-BUTYL ETHER DESORBENT, describes dimethyl sulfoxide and hexane used in liquid-liquid extraction while methyl-butyl ether is used as a desorbent for removing sterols absorbed on the column.

Replacing an environmentally damaging solvent for use in analytical methods and particularly for use in E.P.A.-approved methods for determining oil and grease which in turn would be extremely helpful in the proper design and operation of the nation's wastewater treatment systems is undoubtedly a worthwhile and meritorious goal.

SUMMARY OF THE INVENTION

Accordingly, it is the object of the present invention to provide a novel environmentally acceptable replacement solvent composition which is useful in the gravimetric determination of oil and grease. Another object of the present invention is to find a solvent composition to replace 1,1,2-trichloro-1,2,2-trifluoroethane for use in the gravimetric determination of oil and grease which would be similar in properties to 1,1,2-trichloro-1,2,2-trifluoroethane with respect to volatility, dielectric constant, general solvency, water insolubility, slight toxicity, availability, and cost. Other objects and advantages of the invention will become apparent from the following description.

To solve the problem of using 1,1,2-trichloro-1,2,2-trifluoroethane as the solvent in gravimetric determinations of oil and grease, the present invention proposes to replace 1,1,2-trichloro-1,2,2-trifluoroethane by a novel composition solvent mixture of n-hexane/methyl tertiary-butyl ether. The present invention is virtually devoid of any destructive effect with respect to ozone.

Specifically, the preferred embodiment of the composition to be used according to the invention comprises 80% by volume of n-hexane and 20% by volume of methyl tertiary-butyl ether (MTBE). The composition according to the invention can be used for the same applications and techniques as the 1,1,2-trichloro-1,2,2-trifluoroethane solvent.

Besides replacing an environmentally damaging chlorofluorocarbon, the present novel invention is a mixture of solvents with a specific volume ratio whose boiling point, polarity, dielectric constant and performance characteristics with respect to oil and grease are almost exactly those of 1,1,2-trichloro-1,2,2-trifluoroethane.

Since this set of characteristics does not exist in any single solvent or any heretofore disclosed mixture, significant inventive skill in combining these several diverse characteristics in one mixture was necessary.

The present invention will permit determination of oil and grease in aqueous matrices, such as surface water, saline water, industrial and domestic treatment plant wastewaters, and in solid matrices such as soils, sediment, sludge, biological lipids, mineral hydrocarbons and some industrial wastewaters. Because of its low boiling point, excellent solution of high molecular oil and grease compounds, very low toxicity, availability and reasonable cost, the present invention is an excellent substitute for 1,1,2-trichloro-1,2,2-trifluoroethane especially in light of the mitigation of harmful environmental effects.

The present invention also comprises a process of using this novel composition solvent mixture for the gravimetric determination of oil and grease. It is applicable to the determination of relatively non-volatile hydrocarbons, vegetable oils, animal fats, waxes, soaps, greases and related matter.

DETAILED DESCRIPTION OF THE INVENTION

Figure 1:
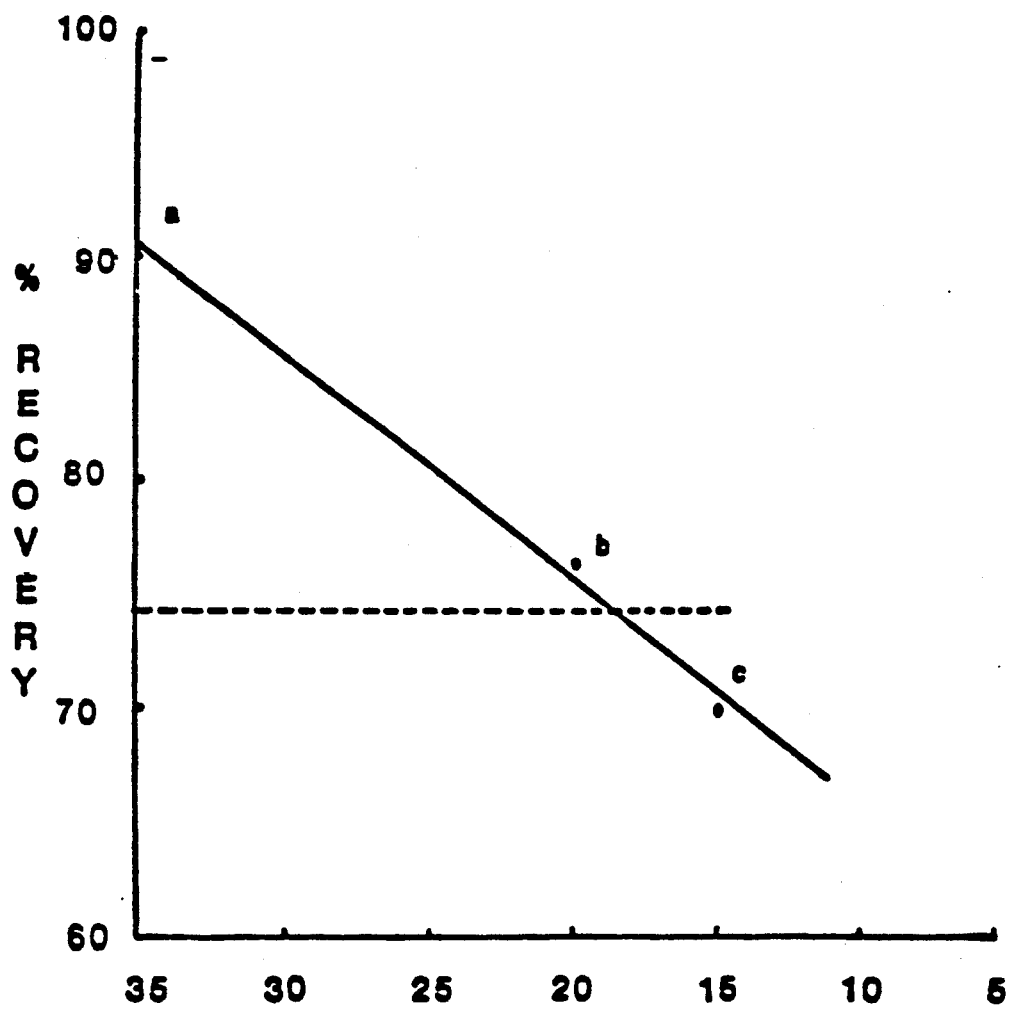
FIG. 1 is a graph of the percentage of recovery of Prudhoe Bay crude in water as a function of the composition of methyl tertiary-butyl ether (MTBE) and hexane.

For the gravimetric method of determination of oil and grease, the selection of a possible replacement solvent for 1,1,2-trichloro-1,2,2-trifluoroethane was made based upon boiling point, dielectric constant and solvation, insolubility in water, toxicity, hazards, availability, and cost. Table 1A lists solvents which are possible candidates to replace 1,1,2-trichloro-1,2,2-trifluoroethane.

Table 1B shows that after screening this listing of 26 solvents for all the requirements mentioned above, methyl tertiary-butyl ether (MTBE) showed characteristics such as a low boiling point necessary for facile evaporation of extract concentrates and a fairly high dielectric constant, when compared to that of hexane, needed for the solvation of refractive oil or grease.

Toxicity is another characteristic criterion considered in the replacement selection. Methyl tertiary-butyl ether with n-hexane (20:80 % by volume) appears to be only slightly toxic when compared to 1,1,2-trichloro-1,2,2-trifluoroethane, according to the $LC_{50}$ rat ihl (inhalation) tests which assist in determining the calculated concentration of a substance in air. [See: Registry of Toxic Effects of Chemical Substances, U.S. Department of Health and Human Services, PHS, CDC, NIOSH, Vol. One and Vol. Two (1980).]

TABLE 1A

| | Hydrocarbons Which Have Some Desirable Features | | | |
|---|---|---|---|---|
| Solvent | Sol. in Water | Boil Pt. °C. | ε, Dielectric Constant | Hazards, Comments |
| Hexane | insol. | 69° | 1.89 (low) | 12, 24, 47, 48, 64 |
| Ethyl ether | 7.5 g/100 g | 34.6° | 4.34 | 24, 47, 57 |
| Methylene Chloride | 2% | 40.2° | 9.08 | 47, 64, $O_3$ |
| Chloroform | Vsl. sol. | 60° | 4.81 | 2, 3, 47, $O_3$ |
| Carbon tetrachloride | Vsl. sol. | 76° H | 2.24 | 2, 14, 15, 47, 48, 49, $O_3$ |
| Carbon disulfide | 0.22 g/100 g | 46° | 2.64 | 5, 24, 27 |
| Hexene-1 | ca. sl. sol. | 63° | ca. 2.05 | 24 |
| Heptene-1 | ca. sl. sol. | 93° H | ca. 2.05 | 24 |
| Cyclopentene | ca. sl. sol. | <49° | 2.20 | 24, 27 |
| Cyclohexene | sl. sol. | 82° H | 2.20 | 24, 47, 64 |
| Cyclopentane | sl. sol. | 49° | 1.965 | 24, 47 |
| Vinyl ether | sl. sol. | 28° | 3.94 | 24 |
| Vinyl acetate | sl. sol. | 72° | — | 44, 52, 64, 69 |
| Ethyl acetate | sl. sol. | 77° H | 6.02 | 44 |
| Ethyl acrylate | — | 99° H | — | — |
| Pentene-1 | 0.04% | 37° | 2.10 | 24, 47, 64 |
| Methyl cyclopentane | V. sl. sol. | 72° | — | 24, 47, 64 |
| Furan | sl. sol. | 32° | — | 24, 47, 64 |
| Methyl t-Butyl ether | sl. sol. | 55° | ca. 4.00 | 24, 47, 64 |
| Thiophene | sl. sol. | 83° | 2.76 | 44, 47, 64, 68 |
| Freon ($CCl_3CF_3$) | insol. | 50° | 4 → 10 | 24, 64, $O_3$ |
| Butanone | sol. | 79° | 18.5 | 24, 64 |
| Benzene | sl. sol. | 80° | 2.27 | 2, 24, 64 |
| Ethyl methyl sulfide | V. sl. sol. | 66° | 5.72 est. | 24 |
| Ethyl sulfide | V. sl. sol. | 91° H | 5.72 | 24 |
| Methyl sulfide | sl. sol. | 37° | 6.2 | 24 |

V. sl. sol. = very slightly soluble.
H = high
est. = estimated
EXPLANATORY LIST FOR NUMBERS USED 2. suspected carcinogen
3. adverse reproductive affects
12. nervous system injury
14. liver damage
15. kidney damage
24. very flammable
47. harmful if inhaled
48. harmful if absorbed (skin)
49. harmful if swallowed
57. explosive peroxides
64. skin and eye irritations
68. stench
69. may polymerize violently
[$O_3$] cl. free radicals generated by action of sunlight upon halogenated compounds function catalytically numerous times in the destruction of ozone found in stratosphere [5b]

TABLE IB
Hydrocarbons-Possible Replacement for Freon

| Solvent | LC$_{50(ihl)}$-Rat (ihl) | Boil Pt. °C. | ε −20° C. Dielectric Constant | Amount of No. 6 Fuel Dissolved; % |
|---|---|---|---|---|
| Ethyl acetate | 1,600 ppm | 77° | 6.02 | 31.71 |
| x Carbon tetra chloride | 4,000 ppm | 76° | 2.238 | — |
| x Chloroform | 8,000 ppm | 60° | 4.80 | 99.95 |
| + Methyl t-butyl ether | 23,576 ppm | 55° | 4.0 | 99.74 |
| o methyl sulfide | 40,250 ppm | 37° | 6.2 | ? |
| x FREON ®-brand chloro fluorocarbon | 87,000 ppm | 50° | ? 4 → 9 | 41.01 |
| x Methyl chloride | 88,000 ppm | 40° | 9.08 | 99.95 |
| + Mixture (35–65) | 70,728 ppm | 55°–69° | 2.59 | — | x Denotes compounds which form free chlorine radicals that decompose catalytically ozone in stratosphere. Listed for comparison.
o Denotes compounds that is not available.
? Value is uncertain
+ For the intended usage, methyl t-butyl ether will be diluted with hexane to one-third its neat concentration; thus the dielectric constant of the methyl t-butyl ether-hexane mixture (35–65) will be approximately 2.59 and the LC$_{50}$-Rat (ihl) will be approximately 70,728 ppm.

Analyses comparing the oil and grease determination results using three different extracting solvents: 1,1,2-trichloro-1,2,2-trifluoroethane; n-hexane; and a mixture of n-hexane/methyl tertiary-butyl ether in the ratio of 80:20, illustrated that a most suitable replacement solvent for 1,1,2-trichloro-1,2,2-trifluoroethane in the gravimetric determination of oil and grease is the present novel composition mixture of n-hexane/methyl tertiary-butyl ether in the ratio of 80:20 (v/v).

In the present invention, aqueous samples containing grease and oil are serially extracted with n-hexane:-methyl tert-butyl ether (MTBE) (80:20, v/v) in a separatory funnel. After separating the aqueous and the solvent layers, the solvent is evaporated and the residue is weighed. This method is suitable for samples that range between 5 and 1000 mg/l of solvent extractable material.

Solid matrices samples are acidified and dried with magnesium sulfate monohydrate or anhydrous sodium sulfate. After drying, the oil and grease are extracted with n-hexane: methyl tertiary-butyl ether (MTBE) (80:20, v/v) using a Soxhlet apparatus. The recycling of the extraction solvent should be the same time period for each of the Soxhlet extractions (4 hours).

Further data gathered from the analyses of wastewater and solid waste dump site samples for oil and grease, which were collected from various different sites selected to be representative of a large number of matrix types, confirm this finding.

EXTRACTABLE OIL AND GREASE GRAVIMETRIC PROCEDURE FOR AQUEOUS MATRICES

This method is used to determine the extractable oil and grease content of aqueous matrices, for example, surface water, saline water, industrial and domestic treatment plant wastewater. It is applicable to the determination of relatively non-volatile hydrocarbons, vegetable oils, animal fats, waxes, soaps, greases and related matter that are extractable by a mixture of n-hexane:-methyl tertiary-butyl ether (MTBE) (80:20, v/v). This method is not applicable to the measurement of light hydrocarbons that volatilize at temperatures below 70° C. Petroleum fuels, from gasoline through No. 2 fuel oils, are completely or partially lost in the solvent removal operation. In addition, heavier residuals of petroleum may contain significant portions of materials that are not extractable with the solvent. This method is suitable for samples that range between 5 and 1000 mg/l of solvent extractable material. Furthermore, this method is entirely empirical and duplicate results can be obtained only by strict adherence to all details of the processes.

The extraction solution n-hexane: methyl tertiary-butyl ether (80:20, v/v) has the ability to dissolve not only oil and grease but also other organic substances. No known solvent will dissolve selectively only oil and grease. It must be noted that surfactant activity in emulsion forming samples appears to trap inorganic drying agents within the organic solvent layer. Drying agents such as sodium sulfate have been found to interfere with the final weight determination. The use of drying agents with this method is *not* recommended.

In the interest of safety, it is necessary to mention that n-hexane can be absorbed through the skin causing adverse effects to the nervous system, including a lack of feeling in the extremities and dizziness. Both n-hexane and methyl tertiary-butyl ether present significant flammability and explosion hazards. Therefore, it is imperative that this solution be mixed fresh daily and used in a fume hood.

Reagent grade chemicals shall be used. Other grades may be used, provided it is first ascertained that the reagent is of sufficiently high purity to permit its use without lessening the accuracy of the determination. The solvents used, n-hexane (C$_6$H$_{14}$) and methyl tert-butyl ether (C$_5$H$_{12}$O) (MTBE), must not leave any measurable residue on evaporation (i.e., 0.1 mg/200 ml); distill if necessary or use the gas chromatographic grade.

Reagent-grade water may be prepared by one of the following techniques. Pass tap water through a carbon filter bed containing about 1 lb of activated carbon. A water purification system may be used to generate organic-free deionized water. The solvent extract of these waters must leave no measurable residue (less than 0.1 mg/200 ml).

Hydrochloric acid (HCl, 6N) may be prepared by adding 12 N HCl (Mallinckrodt), with stirring, to an equal volume of reagent water (1:1, v/v).

Calibration of the analytical balance should be checked at least on a semi-annual basis.

PREPARATION OF SOLVENT MIXTURE

In a fume hood, combine a highly pure grade of n-hexane with a highly pure grade of methyl tertiary-butyl ether in a ratio of 80% n-hexane and 20% methyl tertiary-butyl ether (volume/volume). Store prepared solvent mixture in a dark glass bottle with a TEFLON-®lined screw cap. This mixture must be prepared fresh daily and stored as recommended.

AQUEOUS SAMPLE PREPARATION

Aqueous samples shall be preserved, at the time of collection, by the addition of 6N hydrochloric acid at a rate of 5 mL of acid per liter of sample and stored immediately at 4° C. A solvent blank should accompany each set of samples. The residue from 200 ml of solvent blank should not exceed 0.1 mg upon evaporation to dryness. A duplicate sample and a matrix spike sample are included with each batch of 20 samples or less, starting at the extraction step. Suggested spiking concentration is 20 mg/L using corn oil and mineral oil mixture (50:50).

Because grease may be lost to sampling equipment, the collection of a composite sample is impractical. Individual portions collected at prescribed intervals must be analyzed separately to obtain the average concentration.

EXTRACTION PROCEDURE FOR AQUEOUS MATRICES

Step 1. Mark a sample bottle at the top of the meniscus for later determination of sample volume. Check the pH by touching pH indicator paper to the cap to ensure that the pH is $\leq 2$. Add more acid if necessary. Transfer the contents of the bottle to a separatory funnel.

Note: If more than four hours has lapsed since sample collection, and the sample was not originally acidified, discard the sample.

Step 2. Tare a boiling flask with flat bottom containing boiling chips of silicon carbide (pre-dried in an oven at 103° C. and stored in a desiccator).

Step 3. Add 30 ml n-hexane:methyl tertiary-butyl ether (80:20, v/v) to the sample collection bottle. Rotate the sample bottle to rinse the sides, then transfer the solution to the separatory funnel. Shake gently, vent the separatory tunnel into a hood to release the pressure, repeat until no pressure is noted, then extract by shaking vigorously for 2 min.

Step 4. Allow approximately 10 min for the layers to separate, drain the aqueous layer into a 1500 ml Erlenmeyer flask, then drain the solvent layer into the 250 ml Erlenmeyer. If an emulsion has formed, collect the organic solvent phase plus the emulsion portion in a 250 ml centrifuge bottle. Return the aqueous layer to the separatory funnel.

Step 5. Repeat steps 3 and 4 twice more, combining all organic extracts plus emulsion portions in the 250 ml Erlenmeyer or in the 250 ml centrifuge bottle if emulsions exist.

Step 6. In cases of emulsions, centrifuge both the organic layer and the emulsion layer at 10,000 r.p.m. for 20 minutes. After the centrifuge has stopped, carefully remove the upper organic layer with a pipette. Pipette the solution into a fluted filter paper contained in a glass funnel. The funnel is placed in a tared 125 ml boiling flask containing several boiling chips.

Step 7. If no emulsion forms, filter the combined organic extracts through a fluted filter paper contained in a glass funnel, into a tared 125 ml boiling flask containing several boiling chips. Rinse the 250 ml Erlenmeyer flask or the centrifuge bottle with a total of 10–20 ml additional extraction solvent and transfer it to the fluted filter paper.

Step 8. Connect the boiling flask to the distilling head and evaporate the solvent by immersing the lower half of the flask in a water bath, the temperature of which is 98° C. Due to the size of the flask, it may take two batches or refills to reduce all the solvent. If the extract is split into two batches, additional weighed boiling chips must be added to the second batch. Their weight must be added to the total tare weight of boiling flask and boiling chips. Use gloves to avoid adding fingerprints to the flask.

NOTE: Do not use a hot plate for the distillation step because of the danger of fire and/or explosion when evaporating the ether. Do not use nitrogen or air jet streams to accelerate evaporation!

Step 9. When the solvent appears to be almost evaporated, remove the distilling head, and allow the residual solvent to evaporate in a hood at ambient temperature. Place the flask in a desiccator containing activated silica gel to remove any residual water. Then weigh at 15 minute intervals to a constant weight.

DATA ANALYSIS AND CALCULATIONS

The extractable oil and grease content is measured in mg/L aqueous samples. The following formula is used to make determinations.

$$\text{Recordable oil and Grease} = \frac{\text{Residue} - \text{Blank}}{\text{Amount of Sample } (L)}$$

where: Residue=gross weight of extraction flask with boiling chips minus tare weight with boiling chips, in mg. Blank=residue from evaporation of an equivalent volume of extraction solvent, in mg. (This value should be less than 0.1 mg.)

Amount of Sample=The volume of sample determined by refilling the sample collection bottle to the calibration line and correcting for any acid addition, in L.

EXTRACTABLE OIL AND GREASE GRAVIMETRIC PROCEDURE FOR SOLID MATRICES

This method is used to determine the extractable oil and grease content of solids, for example, soils, biological lipids, mineral hydrocarbons, and some industrial wastewaters. It is used to recover low levels of oil and grease (250 mg/kg) from soil and sediment or (125 mg/kg) from sludge by chemically drying a sample of sludge, soil and sediment, and then extracting via a Soxhlet apparatus. It is applicable to the determination of relatively non-volatile hydrocarbons, vegetable oils, animal fats, waxes, soaps, greases and related matter that are extractable by a mixture of n-hexane:methyl tert-butyl ether (MTBE) (80:20, v/v).

This method is not applicable to the measurement of light hydrocarbons that volatilize at temperatures below 70° C. Petroleum fuels, from gasoline through No. 2 fuel oils, are completely or partially lost in the solvent removal operation. In addition, heavier residuals of petroleum may contain significant portion of materials that are not extractable with the solvent.

This method is also entirely empirical and duplicate results can be obtained only be strict adherence to all details. The previously mentioned requirements for highly pure reagent grade chemicals; solvents not leaving any measurable residue on evaporation; safety precautions and calibration of the analytical balance, all apply. In addition, grease free cotton is required. This can be obtained by extracting non-absorbent cotton with the extraction solvent. The desiccant used in the desiccator is silica gel, 60-200 mesh, activated at 100° C.

Solids shall be stored in sealed glass jars at 4° C. until analysis. Magnesium sulfate monohydrate ($MgSO_4.H_2O$) is prepared by spreading a thin layer of $MgSO_4.7H_2O$ in a dish and drying in an oven at 400° C. for 3 hours. When cool, store the $MgSO_4.H_2O$ in a glass jar.

Sodium sulfate, granular, anhydrous ($Na_2SO_4$) is purified by heating at 400° C. for 4 hours in a shallow tray, or by precleaning the sodium sulfate with methylene chloride. If the sodium sulfate is precleaned with methylene chloride, a method blank must be analyzed, demonstrating that there is no interference from the sodium sulfate. Store in a glass jar.

A solvent blank should accompany each set of samples. The residue from 200 mL of solvent blank should not exceed 0.1 mg upon evaporation to dryness. A duplicate sample and a matrix spike sample are included with each batch of 20 samples or less, starting at the extraction step. Suggested spiking concentration is 625 mg/kg for wet sludge or 1250 mg/kg for soil/sediment using corn oil. Samples may be composited.

PREPARATION OF SOLVENT USED IN EXTRACTION PROCESS

In a fume hood, combine a highly pure grade of n-hexane with a highly pure grade of methyl tertiary-butyl ether in a ratio of 80% n-hexane and 20% methyl tertiary-butyl ether (volume/volume). Store prepared solvent mixture in a dark glass bottle with a TEFLON-®lined screw cap. This mixture must be prepared fresh daily and stored as recommended.

PROCEDURE FOR DETERMINATION OF SAMPLE DRY WEIGHT FRACTION FOR OIL SAMPLES CONTAINING PETROLEUM WITH BOILING POINTS HIGHER THAN NO. 2 FUEL OILS

Weight 5-10 g of the sample into a tared crucible. Determine the dry weight fraction of the sample by drying overnight at 105° C. Allow sample to cool in a desiccator before weighing. The following formula is used to determine the dry weight fraction.

$$\text{dry weight fraction} = \frac{\text{g of dry sample}}{\text{g of sample}}$$

WARNING: The drying oven should be contained in a hood or vented. Significant laboratory contamination may result from a heavily contaminated hazardous waste sample.

NOTE: No. 2 fuel oil in soil will evaporate completely within two hours. These samples must be extracted using the wet sample which is dried with $MgSO_4.1H_2O$. Samples are extracted in the usual manner; weight is determined after being dried in a desiccator using no jet stream.

SAMPLE PREPARATION FOR EXTRACTION

I. Sludge Samples

Weigh out 20±0.5 g of wet sludge. Place in a 150 mL beaker. Acidify to pH 2 with approximately 0.3 mL concentrated HCl. Add 25 g prepared $MgSO_4.H_2O$ and stir to a smooth paste. Spread paste on sides of beaker to facilitate evaporation. Let stand about 15-30 min or until substance is solidified. Remove solids and grind to fine powder in a mortar. Add the powder to the extraction thimble. Wipe beaker and mortar with pieces of filter paper moistened with freshly prepared solvent mixture and add to thimble. Finish filling the thimble with Pyrex glass wool or glass beads.

II. Sediment/Soil Samples

Decant and discard any water layer on a sediment sample. Mix sample thoroughly, especially composited samples. Discard any foreign objects such as sticks, leaves, and rocks. Acidify the sample to pH 2 with approximately 0.3ml. concentrated HCL. Blend 10 g of the soil/sediment sample with 10 g of anhydrous sodium sulfate, and place in an extraction thimble. Finish filling the thimble with PYREX ® glass wool or glass beads.

EXTRACTION PROCEDURE FOR SOLID MATRICES

The Soxhlet extraction apparatus includes a Soxhlet extraction tube, 40 mm ID (may vary depending on manufacturer) with a 45/50 upper joint and a 24/40 lower joint. The rate and time of extraction in the Soxhlet apparatus must be exactly as directed because of varying solubilities of the different greases.

Step 1. Place sufficient n-hexane:methyl tertiary-butyl ether (80:20, v,v) in the 250 ml round bottom boiling flask to allow the Soxhlet apparatus to recycle and extract at a rate of 20 cycles/hour for 4 hours. The extraction thimble must drain freely for the duration of the extraction period.

Step 2. If any turbidity or suspended matter is present in the extraction flask, remove by filtering through grease-free cotton into a 125 ml tared (with boiling chips) boiling flask (pre-dried in an oven at 103° C. and stored in a desiccator). If the extract is clear, transfer it directly to the 125 ml tared (flat bottom) boiling flask. The solvent may have to be evaporated in batches. If the extract is split into two batches, additional boiling chips must be added to the second batch or bumping will occur. Their weight must be added to the total tare weight of boiling flask and boiling chips. Use gloves to avoid adding fingerprints to the flask.

Step 3. Rinse flask and cotton with the solvent mixture.

Step 4. Connect the boiling flask to the Claisen distilling head and evaporate the solvent by immersing the lower half of the flask above the water bath at 98° C.

NOTE: Do not use a hot plate for the distillation step because of the danger of fire and/or explosion when evaporating the ether.

Step 5. When the solvent appears to be almost evaporated, remove the distilling head, and allow the residual solvent to evaporate in a hood at ambient temperature. Place the flask in a desiccator containing activated silica gel to remove any residual (moisture) water, then weight at 15 minute intervals to a constant weight. The length of time required for drying and cooling extracted material must be constant. A gradual increase in weight may result due to the absorption of oxygen; a gradual loss of weight may result due to volatilization.

DATA ANALYSIS AND CALCULATIONS

The extractable oil and grease content is measured in mg/kg. The following formula is used to make determinations.

Recoverable oil and grease =

$$\frac{\text{Residue} - \text{Blank}}{\text{wt. of wet solids (g)} \times \text{dry wt. fraction} \times 1000}$$

where:
Residue = gross weight of extraction flask minus the tare weight, in mg.
Blank = residue from evaporation of an equivalent volume of extraction solvent, in mg. (This value should be less than 0.1 mg.)
Amount of Sample = Weight of wet solids, in g, transferred to the thimble, multiplied by the dry weight fraction and the factor of 1000 to give the weight in kg.

In order that those skilled in the art may better understand the present invention, attention is directed to the following non-limiting Examples, Tables, and Graph. Tables 8, 9, 10–11, 12 and the Recovery Graph contain data gathered from the analyses of wastewater and solid waste dump site samples for oil and grease. The previously described extractable oil and grease gravimetric procedure for aqueous matrices was used for the wastewater samples and the above described extractable gravimetric procedure for solid matrices was employed for the soil samples.

The sole purpose of these analyses was to compare the oil and grease recovery results obtained using three different extracting solvents: 1,1,2-trichloro-1,2,2-trifluoroethane; n-hexane; and a mixture of n-hexane/-methyl tertiary-butyl ether (MTBE) in the ratio of 80:20 (v/v). This work was carried out in an attempt to find a suitable replacement for 1,1,2-trichloro-1,2,2-trifluoroethane as the extracting solvent to determine oil and grease in waste samples.

The samples were collected from three different sites selected to be somewhat representative of a large number of matrix types. The sites were:
1. Cincinnati Wastewater Treatment Plant, Cincinnati, Ohio—primary untreated influent and secondary treated effluent—significant industrial load.
2. Dayton Wastewater Treatment Plant, Dayton, Ohio—primary untreated influent and secondary treated effluent—low industrial load.
3. Waste Dump Sites, Douglasville, Pa.—contaminated soils.

The gravimetric extraction procedure for aqueous matrices was utilized using the influent and effluent samples from Dayton and Cincinnati. All samples from the Dayton and Cincinnati wastewater treatment plants, when mixed with the different extracting solvents, produced thick, stable emulsions.

These samples were serially extracted three times using the present invention solvent mixture, n-hexane: methyl tert-butyl ether (80:20, v/v) as follows:

EXAMPLE I

To 1 liter of prepared water sample, was added 30 mL of n-hexane:methyl tertiary-butyl ether (80:20, v/v). The sample bottle was rotated to rinse the sides. Then the solution was transferred to a separatory funnel. It was shaken vigorously for 2 minutes. Approximately 15 minutes was allowed for the layers to separate. The layers were then separated. The organic solvent phase plus the emulsion portion were collected. The aqueous layer was returned to the separatory funnel and the extraction was repeated in a similar method two additional times. Approximately 100 to 150 ml of liquid was obtained from the combination of the solvent and emulsion portions of the three extractions. This combination solvent/emulsion layer was put in a centrifuge tube and centrifuged at 10,000 r.p.m. for 20 minutes. (Note: The mixture can only be broken into two distinct phases by use of a centrifuge.) After the centrifuge has stopped, most of the upper organic layer was carefully removed with a suction pipette. At the interface a one-eighth inch "felt like" layer remained. The remaining extract layer was removed by using a separatory funnel. The combined organic layer was then filtered through fluted filter paper before distillation on a temperature regulated steam bath above the level of 98° C with the flask portion placed above the water layer of the steam bath. The last portions of the extract contained in the flask were evaporated in a hood without use of an air jet. Then drying was achieved by placing the flask and contents in a desiccator in which was placed five teaspoonsful of silica gel.

Similar extractions of samples were performed using n-hexane as the solvent. In addition, extractions of samples using 1,1,2-trichloro-1,2,2-trifluoroethane were performed. However, for the 1,1,2-trichloro-1,2,2-trifluoroethane centrifuged samples, the top aqueous layer was removed from the centrifuge tube with use of the suction pipette. The organic extract with traces of water was gently transferred to a separatory funnel and the lower 1,1,2-trichloro-1,2,2-trifluoroethane layer separated. The combined organic 1,1,2-trichloro-1,2,2-trifluoroethane extract was passed through a fluted filter paper into a distillation flask before distillation.

Results from the triplicate analyses of wastewater samples from both sampling locations (Cincinnati and Dayton), influents and effluents, were lower when hexane was the extracting solvent than those obtained with 1,1,2-trichloro-1,2,2-trifluoroethane. However, recoveries using hexane/methyl tertiary-butyl ether (80:20) as the solvent, although they were consistently 2–5% higher than the 1,1,2-trichloro-1,2,2-trifluoroethane results, were much more similar to the 1,1,2-trichloro-1,2,2-trifluoroethane results as indicated in Table 8, and the upper part of Table 9. The results from the triplicate analyses of the primary, untreated influent flocculent material taken from the Dayton Wastewater Treatment Plant were exceptions. In this case, the 1,1,2-trichloro-1,2,2-trifluoroethane results were slightly higher than the hexane/methyl tertiary-butyl ether (80:20 v/v) recoveries (see Table 9).

TABLE 8

Total Recoverable Oil and Grease from Waste Water Plant in Cincinnati

| Solvent | Recovered * (mg.) | Mean * (mg.) | SD | RSD |
|---|---|---|---|---|
| Secondary Treated Effluent Before Discharge to River | | | | |
| Hexane | 2.7, 1.4, 1.7 | 1.9 | 0.6 | 35.0% |
| FREON ® | 3.8, 3.4, 4.0 | 3.7 | 0.3 | 8.2% |
| Hexane/MTBE (80:20) | 3.8, 3.4, 4.2, | 3.8 | 0.4 | 10.5% |

$$\frac{\text{Hexane Recovery}}{\text{FREON ® Recovery}} = \frac{1.9}{3.7} = 52\%; \quad \frac{80:20 \text{ Recovery}}{\text{FREON ® Recovery}} = \frac{3.8}{3.7} = 102.7\%$$

TABLE 8-continued

Total Recoverable Oil and Grease from Waste Water Plant in Cincinnati

| Solvent | Recovered * (mg.) | Mean * (mg.) | SD | RSD |
|---|---|---|---|---|
| Primary, Untreated Influent | | | | |
| Hexane | 26.9, 26.0, 24.5 | 25.9 | 1.3 | 4.8% |
| FREON ® | 31.0, 29.3, 27.1 | 29.1 | 2.0 | 6.7% |
| Hexane/MTBE (80:20) | 32.5, 30.1, 29.5 | 30.7 | 1.9 | 5.2% |

$$\frac{\text{Hexane}}{\text{FREON ® Recovery}} = \frac{25.9}{29.1} = 89\%; \frac{80:20 \text{ Recovery}}{\text{FREON ® Recovery}} = \frac{30.7}{29.1} = 105.5\%$$

* Corrected for blanks

TABLE 9

Total Recoverable Oil and Grease from Waste Water Plant in Dayton

| Solvent | Recovered * (mg.) | Mean * (mg.) | SD | RSD |
|---|---|---|---|---|
| Secondary Treated Effluent Before Discharge to River | | | | |
| Hexane | 1.7, 1.8, 1.9 | 1.8 | 0.10 | 5.6% |
| FREON ® | 2.7, 2.4, 2.6 | 2.6 | 0.15 | 6.0% |
| Hexane/MTBE (80:20) | 2.9, 2.7, 2.5 | 2.7 | 0.20 | 7.4% |

$$\frac{\text{Hexane Recovery}}{\text{FREON ® Recovery}} = \frac{1.8}{2.6} = 69\%; \frac{80:20 \text{ Recovery}}{\text{FREON ® Recovery}} = \frac{2.7}{2.6} = 105.5\%$$

| | Primary, Untreated Influent | | | |
|---|---|---|---|---|
| Hexane | 15.5, 12.2, 14.5 | 14.1 | 1.69 | 12.0% |
| FREON ® | 15.1, 13.6, 14.9 | 14.5 | 0.81 | 5.6% |
| Hexane/MTBE (80:20) | 15.4, 13.1, 13.6 | 14.0 | 1.21 | 8.6% |

$$\frac{\text{Hexane}}{\text{FREON ®}} = \frac{14.1}{14.5} = 97\%; \frac{80:20 \text{ Recovery}}{\text{FREON ® Recovery}} = \frac{14.0}{14.5} = 96.5\%$$

EXAMPLE II

The gravimetric extraction procedure for solid matrices was utilized using contaminated soil samples from waste dump sites in Douglasville, Pennsylvania. An analysis was performed to compare oil and grease recovery using three different extracting solvents utilizing a Soxhlet extraction tube. The different extracting solvents tested were 1,1,2-trichloro-1,2,2-trifluoroethane; n-hexane; and a mixture of n-hexane/methyl tertiary-butyl ether in the ratio of 80:20 (v/v). The following procedure using n-hexane:methyl tertiary-butyl ether (80:20 v/v) as the extracting solvent was performed.

Blend 10 grams of the soil sample with 10 grams of anhydrous sodium sulfate and place in an extraction thimble. Finish filling the thimble with PYREX ® glass wool or beads. A sufficient amount of solvent was used to allow the Soxhlet apparatus to recycle and extract at a rate of 20 cycles/hour for 4 hours. After 80 cycles of Soxhlet extractions, any fine carbon particles suspended in the extract were removed by filtering it through grease-free cotton. The solvent is then evaporated using a Claisen distilling apparatus. A water bath at 98° C. temperature was utilized for the distillation. When the majority of the solvent was evaporated, the residual solvent was allowed to evaporate in a hood at ambient temperature.

To remove any residual water, the flask was put in a desiccator containing activated silica gel. It was then weighed at 15 minute intervals to a constant weight.

This Soxhlet extraction procedure was also performed using 1,1,2-trichloro-1,2,2-trifluoroethane and n-hexane, respectively, as the extracting solvents.

Results from the triplicate analyses of waste dump sites for waste oil in soils indicated that after 80 cycles of Soxhlet extractions, hexane and the hexane/methyl tertiary-butyl ether (80:20 v/v) extraction recoveries are similar to those of 1,1,2-trichloro-1,2,2-trifluoroethane. The hexane/methyl tertiarybutyl ether (80:20 v/v) recoveries are slightly higher than the hexane recoveries as indicated in Tables 10 and 11. Similar results were observed when motor oil was extracted with these solvents. It is suspected that motor oil is the contaminant in the soil samples. If the spill contained No. 6 fuel oil, recoveries using hexane as a solvent would be smaller than with 1,1,2-trichloro-1,2,2-trifluoroethane or with hexane/methyl tertiary-butyl ether (80:20 v/v) as the extracting solvent. The No. 6 oil is much less soluble in hexane than it is in hexane/methyl tertiary-butyl ether (80:20 v/v).

TABLE 10

Total Recoverable Oil and Grease from Waste Dump Sites in Douglasville, PA with Solvents on a Dry Weight Basis Determined on Soils Contaminated with Oil (Waste Lubricating Oils)

| Solvents | Recoveries | Mean (%) | SD | RSD% |
|---|---|---|---|---|
| Site #3 | | | | |
| Hexane | 5.56, 5.55, 5.45 | 5.52 | 0.07 | 1.1 |
| FREON ® | 5.35, 5.30, 5.25 | 5.30 | 0.42 | 3.9 |
| Hexane/MTBE (80:20) | 6.09, 5.85, 5.69 | 5.87 | 0.20 | 3.4 |

$$\frac{\text{Hexane Recovery}}{\text{FREON ® Recovery}} = \frac{5.52}{5.30} = 104\%; \frac{80:20 \text{ Recovery}}{\text{FREON ® Recovery}} = \frac{5.87}{5.30} = 110\%$$

| | Site #4 | | | |
|---|---|---|---|---|
| Hexane | 23.73, 23.01, 21.30 | 22.68 | 1.25 | 5.5 |
| FREON ® | 22.84, 22,43, 22.02 | 22.02 | 1.10 | 4.9 |
| Hexane/MTBE (80:20) | 24.99, 24.34, 23.20 | 24.17 | 0.91 | 3.7 |

$$\frac{\text{Hexane}}{\text{FREON ®}} = \frac{22.68}{22.02} = 103\%; \frac{80:20 \text{ Recovery}}{\text{FREON ® Recovery}} = \frac{24.17}{22.02} = 109.8\%$$

| | Site #5 | | | |
|---|---|---|---|---|
| Hexane | 22.46, 21.76, 21.82 | 21.96 | 0.40 | 2.0 |
| FREON ® | 21.16, 21,35, 21.82 | 21.44 | 0.34 | 1.6 |
| Hexane/MTBE (80:20) | 22.92, 22.64, 23.30 | 22.95 | 0.33 | 1.4 |

$$\frac{\text{Hexane Recovery}}{\text{FREON ® Recovery}} = \frac{22.68}{21.44} = 102\%; \frac{80:20 \text{ Recovery}}{\text{FREON ® Recovery}} = \frac{22.95}{21.44} = 107\%$$

EXAMPLE III

Comparative recoveries of oil and grease from samples from various sources—WP024 (60.2% corn oil/39.8 % paraffin oil); Prudhoe Bay Crude; D. B. Wheel Bearing Grease; Petroleum Refining; 5 Wastewater Treatment, ME and Wastewater Treatment, NY—using the described extractive technique with the following different solvents: 1,1,2-trichloro-1,2,2-trifluoroethane;

n-hexane; n-hexane/methyl tertiary-butyl ether (65:35 v/v) and n-hexane/methyl tertiary-butyl ether (80:20 v/v) were performed. The results of which are shown in Table 12.

When the solvent of the instant invention was employed, the amount recovered from one liter samples of the petroleum refinery, the wastewater treatment in ME and the wastewater treatment in NY was maximized. (See lower half of Table 12.)

The graph of FIG. 1 snowing the Recovery of Prudhoe Bay Crude in Water shows various compositions of n-hexane and methyl tertiary-butyl ether used as the solvent in liquid-liquid extractions of 22.4 mg of Prudhoe Bay Crude in 1 liter of reagent water. The dashed line designates recovery when Freon 113 alone is used. The 65%/35% mixture (a) is too strong a solvent; the 15%/85% (c) mixture is too weak a solvent; the 80%/20% mixture (b) best approximates the extraction capabilities when compared with 1,1,2- trichloro-1,2,2-trifluoroethane.

TABLE 12

Comparative Recoveries of Oil and Grease Samples From Various Sources Using Extractive Technique with Different Solvents

| Solvent(s) | Percent Recovery$^d$ | | |
|---|---|---|---|
| | Performance Evaluation WP024 | Prudhoe Bay Crude | DB Wheel Bearing Grease |
| MTBE$^b$ + Hexane (35:65)$^c$ | 101.9 ± 3.1 (3)$^a$ | 90.5 ± 8.4 (3) | 101.2 ± 5.7 (3) |
| FREON ® Hexane | 95.3 ± 2.0 (3) 84.5 ± 3.4 (3) | 73.5 ± 2.1 (3) 65.2 ± 7.9 (3) | 100.8 ± 3.4 (3) 66.3 (2) |

| Solvent(s) | Amount Recovered from One Liter Sample$^e$ | | |
|---|---|---|---|
| | Petroleum Refining | Wastewater Treatment, ME | Wastewater Treatment, NY |
| MTBE + Hexane (20:80) | 6.8 mg (1) | 5.0 mg (1) | 8.2 mg (1) |
| FREON ® Hexane | 4.5 MG (1) 3.3 mg (1) | 4.7 mg (1) 4.4 mg (1) | 6.0 mg (1) 3.7 mg (1) |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A method of dissolving grease and oil using a replacement solvent for 1,1,2-trichloro-1,2,2 trifluoroethane in the gravimetric determination of oil and grease in an aqueous matrix or solid matrix comprising the steps of dissolving said oil or grease using an effective amount of a solvent comprising a mixture of n-hexane and methyl tertiary-butyl ether present in a volume to volume ratio of 80% to 20% respectively to substantially dissolve said oil and grease.

2. A method according to claim 1 wherein said method substantially removes grease and oil from an aqueous matrix.

3. A method according to claim 1 wherein said method substantially removes grease and oil from a solid matrix.

4. A method of gravimetric determination of grease and oil in an aqueous matrix, which comprises the steps of:
    (a) preparing a sample by adding 6 N hydrochloric acid at a rate of 5 ml of acid per liter of sample so that the pH of said sample is ≦2 and storing said prepared sample at 4° C.;
    (b) extracting said prepared sample by using an organic solvent mixture comprising n-hexane:methyl tertiary-butyl ether present in a volume to volume ratio of about 80% to 20% respectively;
    (c) distilling said solvent mixture extraction layer, leaving an extraction residue and residual solvent mixture;
    (d) evaporating any residual solvent mixture from said extraction residue;
    (e) removing any residual water from said extraction residue;
    (f) weighing said extraction residue at 15 minute intervals to a constant weight and
    (g) determining the extractable grease and oil content of said extraction residue.

5. A method according to claim 4 which comprises the additional steps of:
    (a) centrifuging the organic solvent mixture extraction layer and resultant emulsion layer;
    (b) separating off said organic layer and
    (c) filtering said organic layer before distilling said solvent mixture.

6. A method of gravimetric determination of grease and oil in a solid matrix which comprises the steps of:
    (a) preparing a sample by adding concentrated HC until the pH of said sample=2;
    (b) drying said prepared sample by adding prepared $MgSO_4.H_2O$ and allowing sample to solidify;
    (c) grinding said dried solid sample to a powder form;
    (d) adding dried ground sample to an extraction thimble;
    (e) extracting said prepared sample using a Soxhlet extraction apparatus;
    (f) evaporating off said solvent mixture leaving an extracting residue and residual solvent mixture;
    (g) evaporating any residual solvent mixture from said extraction residue;
    (h) removing any residual water from said extraction residue;
    (i) weighing said extraction residue at 15 minute intervals to a constant weight; and
    (j) determining the extractable grease and oil content of said extraction residue.

7. A method according to claim 6 which comprises the additional step of using a sufficient amount of solvent mixture comprising n-hexane:methyl tertiary-butyl ether present in a volume to volume ratio of about 80% to 20% respectively, to allow said Soxhlet apparatus to recycle and extract at a rate of 20 cycles/hour for 4 hours.

8. A method according to claim 6 which comprises the additional step of filtering said extraction liquid through grease free cotton before evaporating off said solvent mixture leaving an extraction residue and residual solvent mixture.

* * * * *